United States Patent

Lavielle et al.

Patent Number: 6,013,667
Date of Patent: Jan. 11, 2000

[54] BENZENESULFONYLAMINE COMPOUNDS, PROCESS FOR PREPARING THEM AND PHARMACEUTICAL COMPOSITIONS

[75] Inventors: Gilbert Lavielle, La Celle Saint Cloud; Bernard Cimetiere, Paris; Tony Verbeuren, Vernouillet; Serge Simonet, Conflans Saint Honorine; Jean-Jacques Descombes, Neuilly-Plaisance, all of France

[73] Assignee: Adir Et Compagnie, Courbevoie, France

[21] Appl. No.: 09/032,587

[22] Filed: Feb. 27, 1998

[30] Foreign Application Priority Data

Feb. 28, 1997 [FR] France ................... 97 02445

[51] Int. Cl.⁷ .................................... A61K 31/21
[52] U.S. Cl. .................. 514/509; 514/510; 514/539; 558/482; 558/488
[58] Field of Search .................. 558/482, 488; 514/510, 509, 539

Primary Examiner—Samuel Barts
Attorney, Agent, or Firm—The Firm of Gordon W. Hueschen

[57] ABSTRACT

Compounds of formula (I):

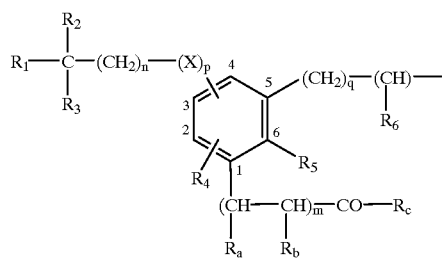

-continued

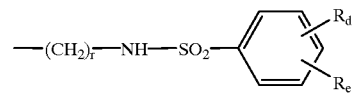

in which:

$R_a$ and $R_b$, identical or different, represent hydrogen or alkyl or together form a bond, $R_C$ represents hydroxyl optionally substituted alkoxy, or optionally substituted amino, $R_1$ represents hydrogen or $-O-NO_2$, $-O-NO$, or $-S-NO$, $R_2$ and $R_3$, identical or different, represent hydrogen, alkyl, or optionally substituted phenyl, X represents oxygen or $-NH-CO-$, m represents 0 or 1, n represents an integer such that $0 \leq n \leq 6$, p represents 0 or 1, $R_4$ represents hydrogen, optionally substituted alkyl, optionally substituted phenyl, or a group as defined in the description, $R_5$ represents hydrogen or alkyl, $R_6$ represents hydrogen or alkyl, or $R_5$ and $R_6$ together form a chain $-(CH_2)_t-$ in which t represents 1 or 2, q represents 0, 1, or 2, r represents an integer such that $0 \leq r \leq 6$, $R_d$ and $R_e$, identical or different, represent hydrogen, halogen, alkyl, alkoxy, hydroxyl, or trihaloalkyl, it being understood that at least one $-O-NO_2$, $O-NO$, or $S-NO$ group is present in $R_1$, $R_4$ or $R_c$; process of preparing same, pharmaceutical compositions thereof, and their use as $TXA_2$-receptor antagonists and NO donors.

21 Claims, No Drawings

BENZENESULFONYLAMINE COMPOUNDS, PROCESS FOR PREPARING THEM AND PHARMACEUTICAL COMPOSITIONS

The present invention relates to novel benzenesulfonylamine derivatives, to a process for their preparation and to the pharmaceutical compositions which contain them.

Besides the fact that they are novel, these compounds possess anti-thromboxane $A_2$ properties as antagonists of thromboxane $A_2$ ($TXA_2$) receptors and, at the same time, NO-donating properties.

$TXA_2$ is a metabolite of arachidonic acid produced by blood platelets and by certain other body cells, which causes considerable constriction of the blood vessels, induces platelet aggregation and has proliferative properties. The production of $TXA_2$ is, inter alia, increased in coronary diseases (e.g. angina pectoris, myocardial infarction) and in cerebrovascular accidents and $TXA_2$ plays a fundamental part in all the processes leading to thrombotic diseases. In addition, this mediator is involved in many other human pathologies such as diabetes, hypertension and atherosclerosis (J. C. Ansquer; STV; 4; 161–167, 1992).

It is thus advantageous to synthesize substances capable of eliminating the proaggregating, vasoconstrictive and proliferative activities of $TXA_2$; in view of the fact that these actions are produced by means of intermediate specific membrane receptors (TP receptors), TP-receptor-antagonist molecules have been synthesized.

Nitrogen monoxide (NO) has recently been discovered as a molecule involved in a wide range of physiological reactions; NO is a vasodilator produced by endothelial cells, an agent which works against the platelet aggregant produced by platelets, a neurotransmitter present in nitridergic neurones and a substance whose production (by NO-synthases) is induced in the body after inflammatory stimuli. In addition, NO also possesses antiproliferative properties Nitro derivatives, such as nitroglycerine, have been used in the treatment of coronary diseases for many decades. The action of its derivatives is based on the fact that these products are NO donors, whose production and/or release is compromised in the diseases. The NO-donor substances are vasodilators and also anti-platelet-aggregant agents (J. S. Stamler, JACC, 1529–1536, 1991; I. Salvemini et al., Biochem. Pharmacol. 44, 17–24, 1992). NO-donor substances are thus useful for cardiovascular pathology involving vasospasms and/or platelet aggregation and/or proliferation.

It was thus particularly advantageous to study substances having the two properties. Indeed, inhibiting the effects of a vasoconstrictive, proaggregating, proliferative substance ($TXA_2$) released in excess in the diseases described and replacing a vasodilatory, anti-aggregant, anti-proliferative substance (NO) whose production and/or release is compromised is a particularly advantageous strategy leading to products which will be capable of restoring a malfunction to the maximum. This strategy effectively leads to the discovery of substances having two independent but synergistic activities in platelets and blood vessels. One considerable advantage of this synergism strategy is that the doses of the NO donor can be relatively low, in order to avoid the excessive hemodynamic consequences usually associated with treatment with nitro derivatives.

The products are thus useful as TP-receptor antagonists and NO donors in the treatment and/or prevention of diseases in which $TXA_2$ is involved and the levels and/or activity of NO are reduced, such as, for example, cardiovascular and cerebrovascular diseases and thrombotic diseases, as well as vascular complications which accompany pathological conditions associated with excessive $TXA_2$ production or activity and/or reduced NO production or activity (e.g. restenosis, vascular complications in diabetes, hypertension, atherosclerosis, Raynaud's disease, kidney disease, lung disease). As TP-receptor antagonists and NO donors, these products also possess properties of protecting the gastric wall (M. L. Ogletree et coll., J. Pharm. Exp. Ther.: 263: 374–380, 1992; S. J. Konturek et al., Scand. J. Gastroenterol.: 30: suppl. 220: 22–27, 1995) and can ben beneficial in impotence (Moncada and Higgs: N. Engl. J. Med: 329: 2002–2012, 1993).

TP-receptor antagonists can also be used in asthma (E. Samara, Cardiovasc. Drug. Rev. 14: 272–282, 1996). By virtue of the inhibitory properties of platelet aggregation, the compounds of the invention can also be proposed in the treatment of migraine (P. Puig-Parellada et al., Prostagland. Leukotr. Essential Fatty acids: 49: 537–547, 1993).

More particularly, the present invention relates to the compounds of formula (I):

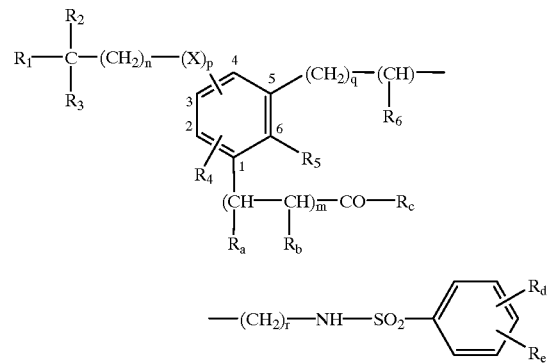

in which:

$R_a$ and $R_b$, which may be identical or different, represent a hydrogen atom or a linear or branched ($C_1$–$C_6$) alkyl group, or alternatively $R_a$ and $R_b$ together form a bond, $R_c$ represents a hydroxyl group, a linear or branched ($C_1$–$C_6$) alkoxy group (optionally substituted with an —O—$NO_2$, —O—NO or —S—NO group) or an amino group (optionally substituted with one or two identical or different, linear or branched ($C_1$–$C_6$) alkyl groups or an optionally substituted phenyl group), $R_1$ represents a hydrogen atom or an —O—$NO_2$, —O—NO or —S—NO group, $R_2$ and $R_3$, which may be identical or different, represent a hydrogen atom or a linear or branched ($C_1$–$C_6$) alkyl group or an optionally substituted phenyl group, X represents an oxygen atom or an —NH—CO— group, m represents 0 or 1, n represents an integer such that $0 \leq n \leq 6$, p represents 0 or 1, $R_4$ represents a hydrogen atom, a linear or branched ($C_1$–$C_6$) alkyl group (optionally substituted with a hydroxyl group), an optionally substituted phenyl group or a group:

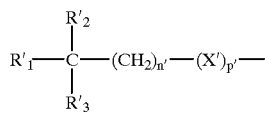

in which:

$R'_1$, represents a hydrogen atom or a group: $-O-NO_2$, $-O-NO$ or $-S-NO$, $R'_2$ and $R'_3$, which may be identical or different, represent a hydrogen atom or a linear or branched ($C_1$–$C_6$) alkyl group or an optionally substituted phenyl group, X' represents an oxygen atom or an $-NH-CO-$ group, n' represents an integer such that $0 \leq n \leq 6$, p' represents 0 or 1, $R_5$ represents a hydrogen atom or a linear or branched ($C_1$–$C_6$) alkyl group, $R_6$ represents a hydrogen atom or a linear or branched ($C_1$–$C_6$) alkyl group, or alternatively $R_5$ and $R_6$ together form a chain $-(CH_2)_t-$ in which t represents 1 or 2, q represents 0, 1 or 2, r represents an integer such that $0 \leq r \leq 6$, $R_d$ and $R_e$, which may be identical or different, represent a hydrogen atom, a halogen atom, a linear or branched ($C_1$–$C_6$) alkyl group, a linear or branched ($C_1$–$C_6$) alkoxy group, a hydroxyl group or a linear or branched ($C_1$–$C_6$) trihaloalkyl group, it being understood that at least one $-O-NO_2$, $-O-NO$ or $-S-NO$ group is present in $R_1$, $R_4$ or $R_c$, the isomers thereof and the addition salts thereof with a pharmaceutically acceptable acid or base.

The preferred compounds of the invention are those for which, taken together or separately:

$R_a$ and $R_b$ each represent a hydrogen atom and m is equal to 1, $R_1$ represents an $-O-NO_2$, $-O-NO$ or $-S-NO$ group, $R_4$ represents a hydrogen atom, $R_5$ and $R_6$ together form a chain $-(CH_2)_t-$, $R_c$ represents a hydroxyl group or a linear or branched ($C_1$–$C_6$) alkoxy group, $R_d$ represents a halogen atom, p is equal to 0, r is equal to 0.

More preferably, the invention relates to the compounds of formula (I) for which $R_1$ represents an $-O-NO_2$ group $R_5$ and $R_6$ together form a chain $-(CH_2)_t$ with t equal to 2 when q is equal to 1, and r is equal to 0, $R_d$ represents a halogen atom when $R_e$ represents a hydrogen, and $R_c$ represents a hydroxyl group or a linear or branched ($C_1$–$C_6$) alkoxy group.

The expression optionally substituted phenyl is understood to mean optionally substituted with one or more identical or different halogen atoms or linear or branched ($C_1$–$C_6$) alkyl, linear or branched ($C_1$–$C_6$) alkoxy, hydroxyl or linear or branched ($C_1$–$C_6$) trihaloalkyl groups.

The invention also covers the process for the preparation of the compounds of formula (I).

The process for the preparation of the derivatives of formula (I) such that p=p'=0 uses as starting material a compound of formula (II):

(II)

in which:

$R_d$, $R_e$, $R_2$, $R_3$, $R_5$, $R_6$, n, q and r have the same meaning as in formula (I), $R_{4a}$ represents a hydrogen atom, a linear or branched ($C_1$–$C_6$) alkyl group (optionally substituted with a hydroxyl group), an optionally substituted phenyl group or a group (in which $R'_2$, $R'_3$ and n' have the same meaning as in formula (I)), and R represents $-CH_2-CH_2-CO_2R'_c$, or $-CO_2R'_c$ (in which $R'_c$ represents a linear or branched ($C_1$–$C_6$) alkyl group optionally substituted with a hydroxyl group), which compound is subjected to a suitable oxidizing treatment, to give the compound of formula (III):

(III)

when p is equal to 0, $R_a$ and $R_b$ each represent a hydrogen atom when m is equal to 1, $R_4$ represents a hydrogen atom, in which:

R, $R_d$, $R_e$, $R_2$, $R_3$, $R_5$, $R_6$, n, q and r have the same meaning as above, $R_{4b}$ represents a hydrogen atom, a linear or branched ($C_1$–$C_6$) alkyl group (optionally substituted with a hydroxyl group), an optionally substituted phenyl group or a group

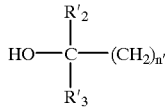

(in which $R'_2$, $R'_3$ and n' have the same meaning as above), which compound of formula (III) is optionally converted, when R represents a group —$CO_2$Alk, into the corresponding aldehyde and then undergoes a Wittig reaction to give a compound of formula (III) in which the group R is replaced by the group —CH=CH—$CO_2R'_c$, which compound of formula (III):

either has its hydroxyl group(s) converted into an OTs group (in which Ts represents the tosyl group) or into a bromine atom, and is subjected to the action of tetrabutylammonium nitrate or silver nitrate, to give the compound of formula (I/a), which is a specific case of the compounds of formula (I):

atom, a linear or branched ($C_1$–$C_6$) alkyl group, an optionally substituted phenyl group or a group

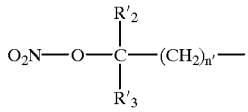

(in which $R'_2$, $R'_3$ and n' have the same meaning as above, and $R'_{c1}$ represents an alkyl group (optionally substituted with an —O—$NO_2$ group)), or is reacted with tert-butyl nitrite to give the compound of formula (I/b), which is a specific case of the compounds of formula (I):

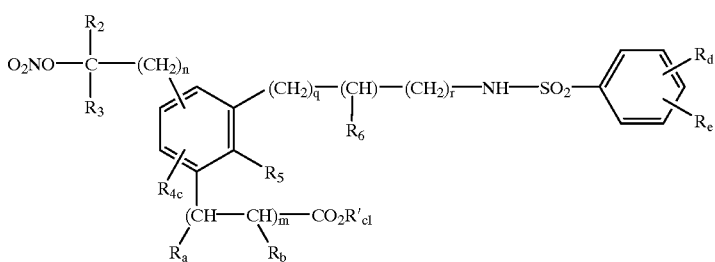

(I/a)

in which:

$R_2$, $R_3$, $R_5$, $R_6$, $R_a$, $R_b$, $R_d$, $R_e$, m, n, q and r have the same meaning as in formula (I), and $R_{4c}$ represents a hydrogen

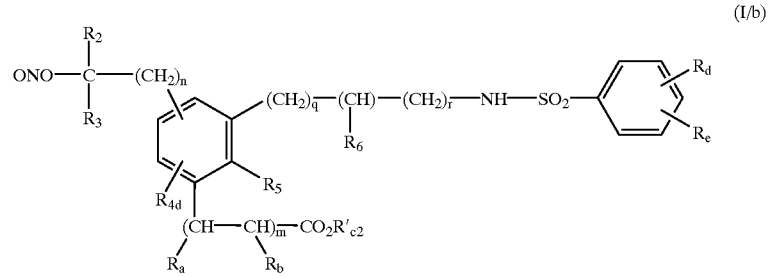

(I/b)

in which $R_2$, $R_3$, $R_5$, $R_6$, $R_a$, $R_b$, $R_d$, m, n, q and r have the same meaning as above, and $R_{4d}$ represents a hydrogen atom, a linear or branched ($C_1$–$C_6$) alkyl group, an optionally substituted phenyl group or a group

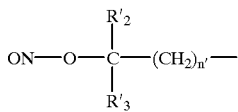

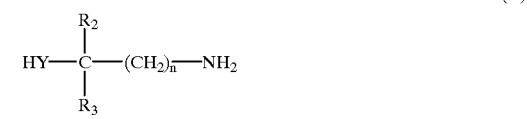

(in which $R'_2$, $R'_3$ and n' have the same meaning as above, and $R'_{c2}$ represents an alkyl group (optionally substituted with an —O—NO group)), which compounds of formula (I/a) or (I/b) have the ester function converted, if so desired, into the corresponding acid or amide function,

- can, where appropriate, be purified according to a standard purification technique,
- have their isomers separated, where appropriate, according to a standard separation technique,
- are converted, if so desired, into the addition salts thereof with a pharmaceutically acceptable acid or base.

In the process for the preparation of the compounds of formula (I) such that p or p' is equal to I and X and X' represent —NH—CO—, the starting material used is a compound of formula (IV):

in which:

$R_2$, $R_3$ and n have the same meaning as in formula (I)

and Y represents a sulfur or oxygen atom, to give the compound of formula (VI):

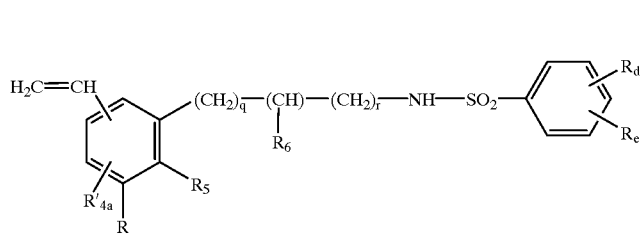

in which:

R, $R_d$, $R_e$, $R_5$, $R_6$, q and r have the same meaning as above, and $R'_{4a}$ represents a hydrogen atom, a linear or branched ($C_1$–$C_6$) alkyl group (optionally substituted with a hydroxyl group), an optionally substituted phenyl group or a vinyl group, the vinyl group(s) of which is(are) converted into formyl group(s) and then into corresponding carboxyl group(s), which compound is reacted with an amine of formula (V):

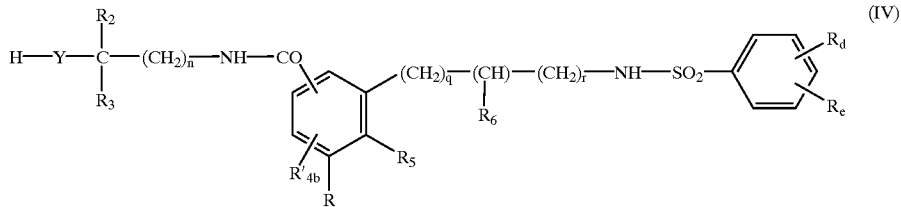

in which:
R, $R_d$, $R_e$, $R_5$, $R_2$, $R_3$, $R_6$, Y, n, q and r have the same meaning as above,
$R'_{4b}$ represents a hydrogen atom, a linear or branched ($C_1$–$C_6$) alkyl group (optionally substituted with a hydroxyl group), an optionally substituted phenyl group or a group 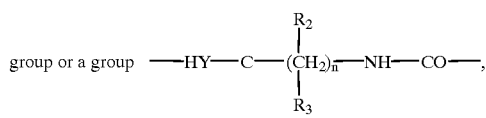

which compound of formula (VI) is optionally converted, when R represents a group —$CO_2$Alk, into the corresponding aldehyde and then undergoes a Wittig reaction to give a compound of formula (VI) in which the group R is replaced by the group —CH=CH—CO₂R'$_c$,
which compound of formula (VI):

either has its hydroxyl group(s) converted into an OTs group (in which Ts represents the tosyl group) or into a bromine atom, and is subjected to the action of tetrabutylammonium nitrate or silver nitrate, to give the compound of formula (I/c), which is a specific case of the compounds of formula (I):

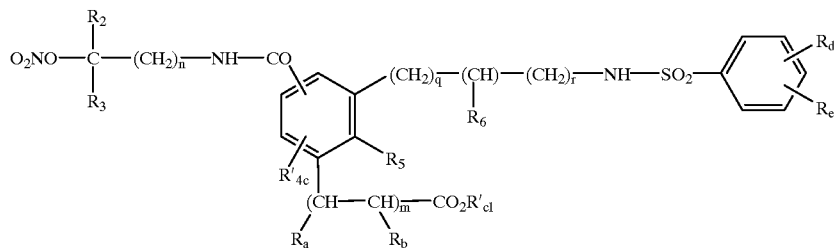

(I/c)

in which:

R$_2$, R$_3$, R$_5$, R$_6$, R$_a$, R$_b$, R$_d$, R$_e$, m, n, q and r have the same meaning as in formula (I), and R'$_{4c}$ represents a hydrogen atom, a linear or branched (C$_1$–C$_6$) alkyl group (optionally substituted with an —O—NO$_2$ group), an optionally substituted phenyl group or a group

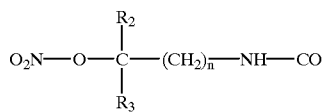

(in which R$_2$, R$_3$ and n have the same meaning as above, and

R'$_{c1}$ represents an alkyl group (optionally substituted with an —O—NO$_2$ group)), or is reacted with tert-butyl nitrite to give the compound of formula (I/d), which is a specific case of the compounds of formula (I):

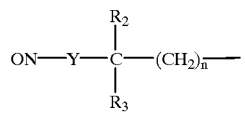

(in which Y, R$_2$, R$_3$ and n have the same meaning as above and R'$_{c2}$ represents an alkyl group (optionally substituted with an —O—NO group)), which compounds of formula (I/c) or (I/d) have their ester function converted, if so desired, into the corresponding acid or amide function, which can, where appropriate, be purified according to a standard purification technique, have their isomers separated, where appropriate, according to a standard separation technique, are converted, if so desired, into the addition salts thereof with a pharmaceutically acceptable acid or base.

In the process for the preparation of the compounds of formula (I) such that X represents an oxygen atom, the starting material used is a compound of formula (VII):

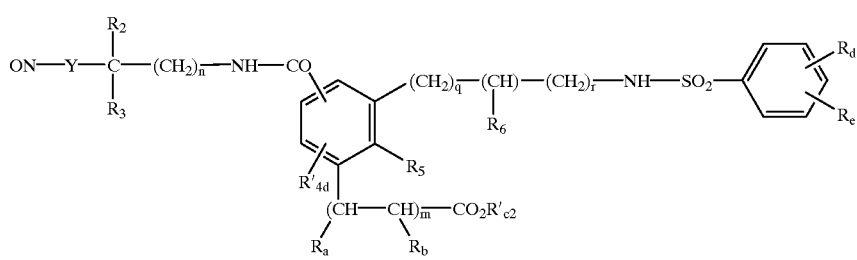

(I/d)

in which:

Y, R$_2$, R$_3$, R$_5$, R$_6$, R$_a$, R$_b$, R$_d$, m, n, q and r have the same meaning as above, and R'$_{4d}$ represents a hydrogen atom, a linear or branched (C$_1$–C$_6$) alkyl group (optionally substituted with an —O—NO group), an optionally substituted phenyl group or a group

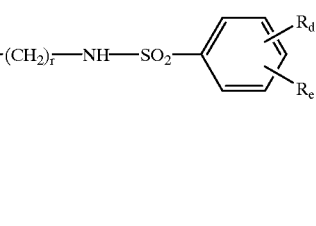

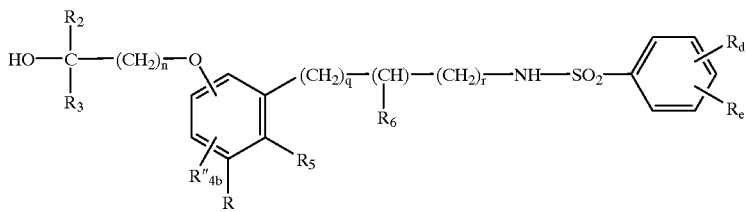
(VII)

in which:

$R_2$, $R_3$, $R_5$, $R_d$, $R_e$, r, q and n are as defined in formula (I), R represents a group

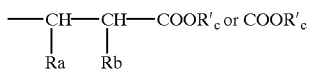

(in which $R'_c$ represents a linear or branched ($C_1$–$C_6$) alkyl group optionally substituted with a hydroxyl group and $R_a$ and $R_b$ are as defined in formula (I)), and $R''_{4b}$ represents a hydrogen atom, a linear or branched ($C_1$–$C_6$) alkyl group, an optionally substituted phenyl group or a group

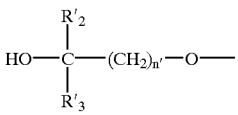

in which n', $R'_2$ and $R'_3$ are as defined in formula (I)), which compound of formula (VII):

either has its hydroxyl group(s) converted into an OTs group (in which Ts represents a tosyl group) or into a bromine atom, and is subjected to the action of tetrabutylammonium nitrate or silver nitrate, to give a compound of formula (I/e), which is a specific case of the compounds of formula (I)

in which:

$R_2$, $R_3$, $R_5$, $R_6$, $R_a$, $R_b$, $R_d$, $R_e$, m, n, q and r have the same meaning as in formula (I), and $R''_{4c}$ represents a hydrogen atom, an alkyl group, an optionally substituted phenyl group or a group

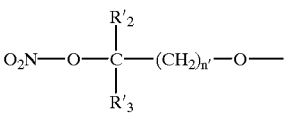

in which $R'_2$, $R'_3$ and n' have the same meaning as above and $R'_{c1}$ represents an alkyl group optionally substituted with an —$ONO_2$ group, or is reacted with tert-butyl nitrite to give the compound of formula (I/f), which is a specific case of the compounds of formula (I):

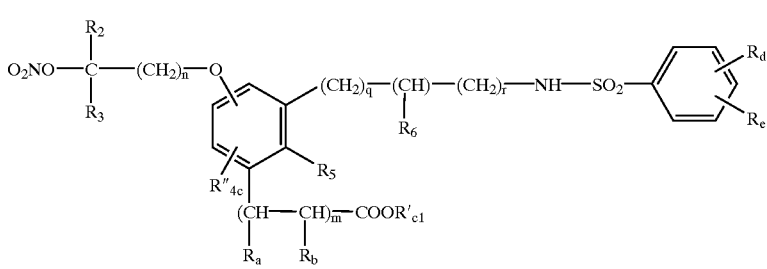
(I/e)

(I/f)

$$\text{ONO}-\underset{R_3}{\overset{R_2}{\underset{|}{C}}}-(CH_2)_{\overline{n}}-O-\underset{\underset{R_a}{|}}{\overset{}{\underset{\text{(CH}-CH)_{\overline{m}}-COOR'_{c2}}{\bigcirc}}}\underset{R_5}{\overset{R''_{4d}}{\bigcirc}}-(CH_2)_{\overline{q}}-(CH)-(CH_2)_{\overline{r}}-NH-SO_2-\bigcirc\underset{R_e}{\overset{R_d}{}}$$

in which:

$R_2, R_3, R_5, R_6, R_a, R_b, R_d, R_e$, n, m, q and r have the same meaning as in formula (I), $R''_{4d}$ represents a hydrogen atom, an alkyl group, an optionally substituted phenyl group or a group $$\text{ONO}-\underset{R'_3}{\overset{R'_2}{\underset{|}{C}}}-(CH_2)_{n'}-O-$$

in which $R'_2$, $R'_3$ and n' have the same meaning as above and $R'_{c2}$ represents an alkyl group optionally substituted with an —O—NO group, which compound of formula (I/e) or (I/f) has its ester function converted, if so desired, into the corresponding acid or amide function, can, where appropriate, be purified according to a standard purification technique, has its isomers separated, where appropriate, according to a standard separation technique, is converted, if so desired, into the addition salts thereof with a pharmaceutically acceptable acid or base.

The invention also covers pharmaceutical compositions containing, as active principle, at least one compound of formula (I) with one or more inert, non-toxic, suitable excipients. Among the pharmaceutical compositions according to the invention, mention may be made more particularly of those which are suitable for oral, parenteral (intravenous or subcutaneous), or nasal administration, simple or sugar-coated tablets, sublingual tablets, gelatin capsules, lozenges, suppositories, creams, ointments, dermal gels, injectable preparations, drinkable suspensions, etc.

The appropriate dosage can be adapted according to the nature and severity of the complaint, the route of administration and the age and weight of the patient. This dosage ranges from 10 to 1000 mg per day in one or more dosage intakes.

The examples which follow illustrate the invention but do not limit it in any way. The starting materials used are starting materials that are known or prepared according to known procedures.

The compounds described in the preparations lead to synthetic intermediates that are useful for the preparation of the compounds of the invention.

Preparation A: Methyl 3-[6-(4-chlorophenylsulfonyl)amino-2-vinyl-5,6,7,8-tetrahydronaphth-1-yl]propanoate Stage A: Ethyl 6-(4-chlorophenylsulfonyl)amino-2-trimethylsilyl-5,6,7,8-tetrahydronaphth-1-ylcarboxylate 290 mmol of 6-(4-chlorophenylsulfonyl)amino-2-oxo-5,6,7,8-tetrahydro-2H-benzo[e]pyran (compound 1) are added to 540 g of ethyl trimethylsilylpropionate. The reaction mixture is brought to 200° C. with stirring. After homogenization, 290 mmol of compound 1 are added and the reaction mixture is stirred at 200° C. up to a new homogenization. A further 290 mmol of compound 1 are then added and the reaction mixture is stirred at 200° C. for 16 hours. The excess ethyl trimethylsilylpropionate is distilled off. The residue is purified by chromatography on a column of silica, using a cyclohexane/ethyl acetate mixture (80/20) as eluent, and the expected product is obtained after crystallization from ether.

Melting point: 104° C.

Stage B: 6-(4-Chlorophenylsulfonyl)amino-2-trimethylsilyl-1-hydroxymethyl-5,6,7,8-tetrahydronaphthalene 645 mmol of lithium aluminum hydride are placed, with stirring, in 350 ml of anhydrous ether. A solution of 28.7 g of aluminum chloride in 700 ml of anhydrous ether is added at room temperature, followed by a solution of 215 mmol of the compound described in the above stage. The mixture is stirred overnight at room temperature. After addition of 100 ml of methanol and filtration of the ammonium salts through Celite, the expected product is obtained.

Stage C: 6-(4-Chlorophenylsulfonyl)amino-2-trimethylsilyl-5,6,7,8-tetrahydronaphth-1-ylcarboxaldehyde To a solution of 90 g of the product obtained in the above stage in 1 l of dichloromethane is added, at room temperature, 239 g of 4-benzylpyridinium dichromate. After stirring for 1 hour at room temperature, the solvent is evaporated off and ethyl acetate is added. The chromium salts precipitate and are filtered off. The filtrate is washed with 0.1 N hydrochloric acid and dried. After purification by chromatography on a column of silica, using a cyclohexane/ethyl acetate mixture (80/20) as eluent, the expected product is obtained.

Stage D: 6-(4-Chlorophenylsulfonyl)amino-2-iodo-5,6,7,8-tetrahydronaphth-1-yl-carboxaldehyde To a solution of 158 mmol of the product obtained in the above stage in 650 ml of dichloromethane is added, at room temperature, 250 ml of a 1 M solution of iodine chloride in dichloromethane. After stirring overnight at room temperature, most of the solvent is evaporated off and ether is added, which causes precipitation of the expected product.

Stage E: 6-(4-Chlorophenylsulfonyl)amino-2-vinyl-5,6,7,8-tetrahydronaphth-1-yl-carboxaldehyde 150 mmol of the product obtained in the above stage, 50 g of vinyltributyltin and 5 g of tetrakis(triphenylphosphine) palladium are maintained at 110° C. for 3 hours, with stirring, in 300 ml of N-methylpyrrolidinone. The solvent is evaporated off and the residue is taken up in 200 ml of dichloromethane and treated with aqueous 10% potassium fluoride solution. After extraction, drying and purification by chromatography on a column of silica, using an ethyl acetate/cyclohexane mixture (80/20) as eluent, 46.2 g of the expected product are obtained.

Stage F: Methyl 3-[6-(4-chlorophenylsulfonyl) amino-2-vinyl-5,6,7,8-tetrahydronaphth-1-yl]prop-2-enoate 123 mmol of the compound obtained in the above stage and 50 g of (carbomethoxymethylidene) triphenylphosphorane are maintained at reflux for 3 hours in 300 ml of toluene. After evaporation of the solvent and purification of the residue by chromatography on a column of silica, using a cyclohexane/ethyl acetate mixture (50/50) as eluent, the expected product is obtained.

Stage G: Methyl 3-[6-(4-chlorophenylsulfonyl) amino-2-vinyl-5,6,7,8-tetrahydronaphth-1-yl] propanoate To 2400 ml of a stirred 0.1 N solution of samarium iodide in THF is added a solution of 123 mmol of the compound obtained in the above stage. The mixture is stirred for 1 hour at room temperature. After addition of 150 ml of anhydrous methanol, the mixture is stirred overnight. The solvent is then evaporated off and the residue is taken up in dichloromethane and washed with 0.1 N hydrochloric acid. The organic phases are dried and, after purification by column chromatography using a cyclohexane/ethyl acetate mixture (80/20) as eluent, the expected product is obtained after recrystallization from ether.

Melting point: 138° C.

Preparation B: Methyl 3-[6-(4-chlorophenylsulfonyl)amino-3-vinyl-5,6,7,8-tetrahydronaphth-1-yl]propanoate Stage A: Ethyl 3-bromo-6-(4-chlorophenylsulfonyl) amino-2-trimethylsilyl-5,6,7,8-tetrahydronaphth-1-ylcarboxylate The expected product is obtained according to the process described in stage A of preparation A, using 3-bromo-6-(4-chlorophenylsulfonyl)amino-2-oxo-5,6,7,8-tetrahydro-2H-benzo[e]pyran as starting material.

Melting point: 134° C.

Stage B: Ethyl 3-bromo-6-(4-chlorophenylsulfonyl) amino-5,6,7,8-tetrahydronaphth-1-ylcarboxylate 73 mmol of the compound described in the above stage are refluxed for 4 hours in 300 ml of trifluoroacetic acid. After evaporation of the acid, the residue is purified by column chromatography using a cyclohexane/ethyl acetate mixture (80/20) as eluent, and gives the expected product.

Stage C: 3-Bromo-6-(chlorophenylsulfonyl)amino-1-hydroxymethyl-5,6,7,8-tetrahydronaphthalene The expected product is obtained according to the process described in stage B of preparation A, starting with the compound obtained in the above stage.

Stage D: 3-Bromo-6-(chlorophenylsulfonyl)amino-5,6,7,8-tetrahydronaphth-1-yl-carboxaldehyde The expected product is obtained according to the process described in stage C of preparation A, starting with the compound obtained in the above stage.

Melting point: 145° C.

Stage E: Methyl 3-[3-bromo-6-(4-chlorophenylsulfonyl)amino-5,6,7,8-tetrahydronaphth-1-yl]prop-2-enoate To a solution of 30 mmol of the expected product of the above stage in 200 ml of toluene are added 12 g of (carbomethoxymethylidene)triphenylphosphorane. The solution is refluxed for 3 hours. After evaporation of the solvent and purification of the residue by chromatography on a column of silica, using a cyclohexane/ethyl acetate mixture (50/50) as eluent, the expected product is obtained.

Stage F: Methyl 3-[3-bromo-6-(4-chlorophenylsulfonyl)amino-5, 6,7,8-tetrahydronaphth-1-yl]propanoate To a solution of 35 mmol of the product obtained in the above stage in 100 ml of methanol are added 2.10 g of cobalt chloride hexahydrate, followed by portionwise addition of 2.66 g of sodium borohydride. The reaction mixture is stirred for 2 hours at room temperature and then filtered. The solvent is evaporated off. The residue is purified by chromatography on a column of silica, using a cyclohexane/ethyl acetate mixture (80/20) as eluent, and gives the expected product after crystallization from ether.

Melting point: 110° C.

Stage G: Methyl 3-[6-(4-chlorophenylsulfonyl) amino-3-vinyl-5,6,7,8-tetrahydronaphth-1yl] propanoate The expected product is obtained according to the process described in stage E of preparation A, starting with the compound described in the above stage.

Preparation C: tert-Butyl 3-{6-[(4-chlorophenylsulfonyl)amino]-3-vinyl-5,6,7,8-tetrahydronaphth-1-yl}propanoate The expected product is obtained according to the process described in preparation B, replacing in stage E the (carbomethoxymethylidene)triphenylphosphorane by (carbo-tert-butoxymethylidene) triphenylphosphorane.

Preparation D: Methyl 3-{6-[(4-chlorophenylsulfonyl) amino]-2-(2-hydroxyethyl)-5, 6,7,8-tetrahydronaphth-1-yl}prop-2-enoate Stage A: {6-[(4- Chlorophenylsulfonyl)amino]-2-(2-hydroxyethyl)-5,6,7,8-tetrahydronaphth-1-yl}carboxaldehyde To 7.6 mmol of the compound described in preparation A, stage E, in 35 ml of THF are added 20 ml of a 1 M solution of borate/tetrahydrofuran complex in THF. After stirring for 2 hours at room temperature, the solution is cooled to 0° C. and 8.5 ml of water are added, followed by 7.6 g of sodium perborate tetrahydrate.

After stirring overnight the THF is evaporated off and the residue is taken up in dichloromethane and then extracted. The organic phase is dried, concentrated and purified by chromatography from silica gel, using an ethyl acetate/cyclohexane mixture (50/50) as eluent, to give the expected compound.

Stage B: Methyl 3-{6-[(4chlorophenylsulfonyl) amino]-2-(2hydroxyethyl)-5,6,7,8-tetrahydronaphth-1-yl}prop-2-enoate The expected product is obtained according to the process described in preparation A, stage F, starting with the compound described in the above stage.

Preparation E: Methyl 3-{6-[(4-chlorophenylsulfonyl) amino]-3-(2-hydroxyethyl)-5,6,7,8-tetrahydronaphth-1-yl}prop-2-enoate Stage A: {6-[(4-Chlorophenylsulfonyl)amino]-3-vinyl-5,6,7,8-tetrahydronaphth-1-yl}carboxaldehyde The expected product is obtained according to the process described in preparation A, stage E, starting with the compound described in preparation B, stage D.

Stage B: {6-[(4-Chlorophenylsulfonyl)amino]-3-(2-hydroxyethyl)-5,6,7,8-tetrahydronaphth-1-yl}carboxaldehyde The expected product is obtained according to the process described in preparation D, stage A, starting with the compound described in the above stage.

Stage C: Methyl 3-{6-[(4-chlorophenylsulfonyl)amino]-3-(2-hydroxyethyl)-5,6,7,8-tetrahydronaphth-1-yl}prop-2-enoate The expected product is obtained according to the process described in preparation A, stage F, starting with the compound described in the above stage.

Preparation F: Methyl 3-{3-allyl-6-[(4-chlorophenylsulfonyl)amino]-5,6,7,8-tetrahydronaphth-1-yl}propanoate The expected product is obtained according to the process described in preparation B, replacing, in stage G, the vinyltributyltin by allyltributyltin.

Preparation G: Ethyl 3-{6-[(4-chlorophenylsulfonyl)amino]-3-vinyl-5,6,7,8-tetrahydronaphth-1-yl}carboxylate The expected product is obtained according to the process described in preparation A, stage E, starting with the compound described in preparation B, stage B.

Preparation H: Methyl 3-{6-[(4-chlorophenylsulfonyl)amino]-2-(2-hydroxyethoxy)-5,6,7,8-tetrahydronaphth-1-yl}propanoate Stage A: {6-[(4-Chlorophenylsulfonyl)amino]-2-hydroxy-5,6,7,8-tetrahydronaphth-1-yl}carboxaldehyde The expected product is obtained according to the process described by Vollhart (Angew Chem. Int. Eng., 1984, p. 539) starting with the compound described in preparation A, stage C.

Stage B: {6-[(4-Chlorophenylsulfonyl)amino]-2-(2-hydroxyethoxy)-5,6,7,8-tetrahydronaphth-1-yl}carboxaldehyde A solution of 2 mmol of the compound described in the above stage in 25 ml of acetone is refluxed in the presence of 3.8 mmol of potassium carbonate for 10 minutes. 3.8 mmol of 2-bromoethanol are then added and the medium is refluxed for 6 hours. After cooling and filtration, the filtrate is concentrated. The residue obtained is taken up in an ethyl acetate/water mixture and extracted. The organic phase is washed with 20% sodium hydroxide solution and then with saturated aqueous sodium chloride solution, dried and concentrated to give the expected compound.

Stage C: Methyl 3-{6-[(4-chlorophenylsulfonyl)amino]-2-(2-hydroxyethoxy)-5,6,7,8-tetrahydronaphth-1-yl}propanoate The expected product is obtained according to the process described in preparation A, stages F and G, starting with the compound described in the above stage.

Preparation I: Methyl 3-{6-[(4-chlorophenylsulfonyl)amino]-2,3-bisvinyl-5,6,7,8-tetrahydronaphth-1-yl}propanoate Stage A: Ethyl 3-{3-bromo-6-[(4-chlorophenylsulfonyl)amino]-2-iodo-5,6,7,8tetrahydronaphth-1-yl}carboxylate The expected product is obtained according to the process described in preparation A, stage D, starting with the compound described in preparation B, stage A.

Stage B: {3-Bromo-6-[(4-chlorophenylsulfonyl)amino]-2-iodo-5,6,7,8-tetrahydronaphth-1-yl}carboxaldehyde The expected product is obtained according to the process described in preparation A, stages B and C, starting with the compound described in the above stage.

Stage C: Methyl 3-{3-bromo-6-[(4-chlorophenylsulfonyl)amino]-2-iodo-5,6,7,8-tetrahydronaphth-1-yl}propanoate The expected product is obtained according to the process described in preparation A, stages F and G, starting with the compound described in the above stage.

Stage D: Methyl 3-{6-[(4-chlorophenylsulfonyl)amino]-2,3-bisvinyl-5,6,7,8tetrahydronaphth-1-yl}propanoate The expected product is obtained according to the process described in preparation A, stage E, starting with the compound described in the above stage, taking care to follow the stoichiometry.

Preparation J: Vinyl 3-{6-[(4-chlorophenylsulfonyl)amino]-2-vinyl-5,6,7,8-tetrahydronaphth-1-yl}propanoate The expected product is obtained by a transesterification reaction using the vinyl alcohol (prepared in situ by the method described by Rodler et al. J. Am. Chem. Soc., 1984, 106, 4029) of the compound described in preparation B.

Preparation K: Methyl 3-{6-[(4-chlorophenylsulfonyl)aminoethyl]-2-vinyl-5,6,7,8-tetrahydronaphth-1-yl}propanoate The expected product is obtained according to the process described in preparation A, starting with 6-(4-chlorophenylsulfonyl)aminoethyl-2-oxo-5,6,7,8-tetrahydro-2H-benzo[e]pyran.

Preparation L: Methyl 3-{6-[(4-fluorophenylsulfonyl)amino]-2-vinyl-5,6,7,8-tetrahydronaphth-1-yl}propanoate The expected product is obtained according to the process described in preparation A, starting with 6-(4-fluorophenylsulfonyl)amino-2-oxo-5,6,7,8-tetrahydro-2H-benzo[e]pyran.

Preparation M: Methyl 3-{[6-toluylsulfonyl)amino]-2-vinyl-5,6,7,8-tetrahydronaphth-1-yl}propanoate The expected product is obtained according to the process described in preparation A, starting with 6-toluylsulfonylamino-2-oxo-5,6,7,8-tetrahydro-2H-benzo[e]pyran.

Preparation N: Methyl 3-{5-{2-[(4-chlorophenylsulfonyl)amino]ethyl}-2-vinylphenyl}propanoate Preparation O: Methyl 3-{5-{2-[(4-chlorophenylsulfonyl)amino]ethyl}-3-vinylphenyl}propanoate

EXAMPLE 1

Methyl 3-{[6-(4-chlorophenylsulfonyl)amino]-2-(2-nitroxyethyl)-5,6,7,8-tetrahydronaphth-1-yl}propanoate Stage A: Methyl 3-[6-(4-chlorophenylsulfonyl)amino-2-(2-hydroxyethyl)-5,6,7,8-tetrahydronaphth-1-yl]propanoate To 11.5 mmol of the compound described in preparation A in 50 ml of THF are added 25 ml of a 1 M solution of borane/tetrahydrofuran complex in THF. After stirring for 2 hours at room temperature, the solution is cooled to 0° C. and 12.5 ml of distilled water are added, followed by 11.5 g of sodium perborate tetrahydrate. After stirring overnight, the THF is evaporated off. After extraction with dichloromethane, drying and evaporation of the solvent, the residue is purified by chromatography on a column of silica, using an ethyl acetate/cyclohexane mixture (50/50) as eluent, and gives the expected product.

Melting point: 132° C.

Stage B: Methyl 3-[6-(4-chlorophenylsulfonyl)amino-2-(2-tosyloxyethyl)-5,6,7,8tetrahydronaphth-1-yl]propanoate To 2.41 mmol of the compound obtained in the above stage in 20 ml of dichloromethane are added 0.8 ml of pyridine and then 0.92 g of tosyl chloride. After stirring overnight at room temperature, the mixture is washed with 1 N hydrochloric acid and dried. After evaporation of the solvent and purification by chromatography on a column of silica, using a cyclohexane/ethyl acetate mixture (70/30) as eluent, the expected product is obtained.

Stage C: Methyl 3-[6-(4-chlorophenylsulfonyl)amino-2-(2-nitroxyethyl)-5,6,7,8tetrahydronaphth-1-yl]propanoate 10.4 mmol of the compound described in the above stage and 0.47 g of tetrabutylammonium nitrate are refluxed for 2 hours in 50 ml of toluene. After evaporation of the toluene and purification by chromatography on a column of silica, using a cyclohexane/ethyl acetate mixture (70/30) as eluent, the expected product is obtained.

EXAMPLE 2

3-{6-[(4-Chlorophenylsulfonyl)amino]-2-(2-nitroxyethyl)-5,6,7,8-tetrahydronaphth-1-yl}propionic acid 7.97 mmol of the compound described in Example 1 are refluxed for 2 hours in 20 ml of methanol in the presence of 1.6 ml of 1 N sodium hydroxide. The solution is filtered, most of the methanol is evaporated off and 10 ml of water are added, followed by 1 N hydrochloric acid until the pH=1. The precipitate obtained is dried and recrystallized in ether and gives the expected compound.

Melting point: 175° C. (dec)

EXAMPLE 3

Methyl 3-[6-(4-chlorophenylsulfonyl)amino-2-nitroxymethyl-5,6,7,8-tetrahydronaphth-1-yl]propanoate Stage A: Methyl 3-[6-(4-chlorophenylsulfonyl)amino-2-hydroxymethyl-5,6,7,8tetrahydronaphth-1-yl]propanoate 2 g of the product described in preparation A are subjected to ozonolysis at −78° C. in 150 ml of dichloromethane. After 2 hours at −78° C., 150 ml of methanol are added, followed by slow addition of 5 g of sodium borohydride. The reaction mixture is brought to room temperature and stirred overnight. After addition of saturated aqueous sodium bicarbonate solution and evaporation of most of the methanol, the reaction mixture is extracted with dichloromethane. The organic phase is dried and evaporated. Purification by chromatography on a column of silica, using an ethyl acetate/cyclohexane mixture (50/50) as eluent, gives the expected product.

Stage B: Methyl 3-[6-(4-chlorophenylsulfonyl)amino-2-bromomethyl-5,6,7,8tetrahydronaphth-1-yl]propanoate To a solution of 2.68 g of triphenylphosphine in 50 ml of dichloromethane is added, at room temperature, a solution of 2.12 g of carbon tetrabromide in 25 ml of dichloromethane. The yellow solution is stirred for 15 minutes and a solution of 1.77 g of the product described in the above stage in 50 ml of dichloromethane is added. After stirring at room temperature for 1 hour, the solvent is evaporated off. Purification by chromatography on a column of silica, using a cyclohexane/ethyl acetate mixture (80/20) as eluent, gives the expected product.

Stage C: Methyl 3-[6-(4-chlorophenylsulfonyl)amino-2-nitroxymethyl-5,6,7,8tetrahydronaphth-1-yl]propanoate To a solution of 1 mmol of the product obtained in the above stage in 10 ml of acetonitrile is added a solution of 250 mg of silver nitrate in 10 ml of acetonitrile. After stirring at room temperature overnight, the silver bromide precipitate is filtered off. The solvent is evaporated off and purification by chromatography on a column of silica, using a cyclohexane/ethyl acetate mixture (80/20) as eluent, gives the expected product.

EXAMPLE 4

3-[6-(4-Chlorophenylsulfonyl)amino-2-nitroxymethyl-5,6,7,8-tetrahydronaphth-1-yl]propionic acid The expected product is obtained according to the process described in Example 2, starting with the compound obtained in Example 3.

EXAMPLE 5

Methyl 3-{6-[(4-chlorophenylsulfonyl)amino]-3-(2-nitroxyethyl)-5,6,7,8-tetrahydronaphth-1-yl}propanoate Stage A: Methyl 3-{6-[(4-chlorophenylsulfonyl)amino]-3-(2-hydroxyethyl)-5,6,7,8-tetrahydronaphth-1-yl}propanoate The expected product is obtained according to the process described in stage A of Example 1, starting with the compound described in preparation B.

Stage B: Methyl 3-{6-[(4-chlorophenylsulfonyl)amino]-3-(2-tosyloxyethyl)-5,6,7,8-tetrahydronaphth-1-yl}propanoate The expected product is obtained according to the process described in stage B of Example 1, starting with the compound obtained in the above stage.

Stage C: Methyl 3-[6-(4-chlorophenylsulfonyl)amino-3-(2-nitroxyethyl)-5,6,7,8-tetrahydronaphth-1-yl]propanoate The expected product is obtained according to the process described in stage C of Example 1, starting with the compound obtained in the above stage.

EXAMPLE 6

3-{6-[(4-Chlorophenylsulfonyl)amino]-3-(2-nitroxyethyl)-5,6,7,8-tetrahydronaphth-1-yl}propionic acid The expected product is obtained according to the process described in Example 2, starting with the compound obtained in Example 5.

EXAMPLE 7

Methyl 3-{6-[(4-chlorophenylsulfonyl)amino]-2-(2-nitrosothio-2-methylpropylcarbamoyl)-5,6,7,8-tetrahydronaphth-1-yl}propanoate Stage A: Methyl 3-{6-[(4-chlorophenylsulfonyl)amino]-2-formyl-5,6,7,8tetrahydronaphth-1-yl}propanoate To a solution of 23 mmol of the product described in preparation A, in a mixture of 100 ml of dioxane and 50 ml of water, are added, at room temperature, 2.5 g of a solution of osmium tetroxide in 2-methyl-2-propanol, followed by 20 g of sodium periodate. After stirring overnight at room temperature, the suspension is filtered and the filtrate is evaporated. The oil obtained is taken up in dichloromethane and this organic phase is washed with water, dried and evaporated. The residue is purified by chromatography on a column of silica, using a cyclohexane/ethyl acetate mixture (60/40) as eluent, and gives the expected product.

Melting point: 110° C.

Stage B: 6-(4-Chlorophenylsulfonyl)amino-1-(2-methoxycarbonylethyl)-5,6,7,8-tetrahydronaphthalene-2-carboxylic acid To a solution of 6.88 mmol of the product obtained in the above stage in 30 ml of acetone is added, at room temperature, a solution of 2.7 g of potassium permanganate in 50 ml of an acetone/water mixture (50/50). The solution is stirred for 2 hours at room temperature. After filtration, 100 ml of methanol are added and the solution is refluxed for 2 hours. After filtration and evaporation of the solvent, 100 ml of water are added. After acidification to pH=2, extraction with dichloromethane, drying and evaporation of the solvent, purification of the residue by chromatography on a column of silica, using a dichloromethane/methanol mixture (95/5) as eluent, gives the expected product.

Stage C: Methyl 3-[6-(4-chlorophenylsulfonyl)amino-2-(2-mercapto-2-methylpropylcarbamoyl)-5,6,7,8-tetrahydronaphth-1-yl]propanoate The expected product is obtained according to the process described in J. Org. Chem., 59, 7019–7026, (1994). To a solution of 4.97 mmol of the product described in the above stage in 50 ml of benzene are added 5 ml of thionyl chloride. After refluxing for 1 hour, the solution is evaporated to dryness to give the corresponding acid chloride. To a solution of 0.75 g of 1-amino-2-methyl-2-propanethiol chloride in 50 ml of acetonitrile are added, at room temperature, 3 ml of N,N-diisopropylethylamine, followed by a solution of the above acid chloride in 50 ml of acetonitrile. After stirring for 30 minutes at room temperature, hydrolysis, extraction with dichloromethane, drying and evaporation of the solvent, the residue is purified by chromatography on a column of silica, using an ethyl acetate/cyclohexane mixture (30/70) as eluent, to give the expected product.

Stage D: Methyl 3-{6-[(4-chlorophenylsulfonyl)amino]-2-(2-nitrosothio-2-methylpropylcarbamoyl)-5,6,7,8-tetrahydronaphth-1-yl}propanoate To a solution of 1.06 g of the product obtained in the above stage in 25 ml of dichloromethane is added, at room temperature, 0.3 g of tert-butyl nitrite. After stirring for 15 minutes at room temperature, evaporation of the solvent gives the expected product.

EXAMPLE 8

3-{6-[(4-Chlorophenylsulfonyl)amino]-2-(2-nitrosothio-2-methylpropylcarbamoyl)-5,6,7,8-tetrahydronaphth-1-yl}propionic acid The expected product is obtained according to the process described in Example 2, starting with the compound described in Example 7.

EXAMPLE 9

Methyl 3-{6-[(4-chlorophenylsulfonyl)amino]-3-nitroxymethyl-5,6,7,8-tetrahydronaphth-1-yl}propanoate The expected product is obtained according to the process described in Example 3, starting with the compound obtained in preparation B.

EXAMPLE 10 tert-Butyl 3-{6-[(4-chlorophenylsulfonyl)amino]-3-nitroxymethyl-5,6,7,8-tetrahydronaphth-1-yl}propanoate Stage A: tert-Butyl 3-{6-[(4-chlorophenylsulfonyl)amino]-3-formyl-5,6,7,8-tetrahydronaphth-1-yl}propanoate The expected product is obtained according to the process described in Example 7, stage A, starting with the compound described in preparation C.

Stage B: tert-Butyl 3-{6-[8(4-chlorophenylsulfonyl)amino]-3-hydroxymethyl-5,6,7,8-tetrahydronaphth-1-yl}propanoate To a solution of 6.5 mmol (3 g) of the product of the above stage in 50 ml of methanol are added, at room temperature, 26.4 mmol (1 g) of sodium borohydride. The reaction mixture is stirred for 30 minutes at room temperature. After addition of saturated aqueous sodium bicarbonate solution and evaporation of most of the methanol, the reaction mixture is extracted with dichloromethane. The organic phase is dried and evaporated. Purification by chromatography on a column of silica, using an ethyl acetate/cyclohexane mixture (50/50) as eluent, gives the expected product.

Stage C: tert-Butyl 3-{6-[(4-chlorophenylsulfonyl)amino]-3-bromomethyl-5,6,7,8-tetrahydronaphth-1-yl}propanoate The expected product is obtained according to the process described in Example 3, stage B, starting with the compound described in the above stage.

Stage D: tert-Butyl 3-{6-[(4-chlorophenylsulfonyl)amino]-3-nitroxymethyl-5,6,7,8-tetrahydronaphth-1-yl}propanoate The expected product is obtained according to the process described in Example 3, stage C, starting with the compound described in the above stage.

EXAMPLE 11

3-{6-[(4-Chlorophenylsulfonyl)amino]-3-nitroxymethyl-5,6,7,8-tetrahydronaphth-1-yl}propionic acid Method A The expected product is obtained according to the process described in Example 2, stage A, starting with the compound described in Example 9.

Method B

Hydrogen chloride gas is bubbled into a solution of 0.1 g of the compound described in Example 10 in 20 ml of anhydrous ether. Evaporation of the solvent gives the expected product.

EXAMPLE 12

Methyl 3-{6-[(4-chlorophenylsulfonyl)amino]-2-(2-nitroxyethyl)-5,6,7,8-tetrahydronaphth-1-yl}prop-2-enoate Stage A: Methyl 3-{6-[(4-chlorophenylsulfonyl)amino]-2-(2-tosyloxyethyl)-5,6,7,8-tetrahydronaphth-1-yl}prop-2-enoate The expected product is obtained according to the process described in Example 1, stage B, starting with the compound described in preparation D.

Stage B: Methyl 3-{6-[(4-chlorophenylsulfonyl)amino]-2-(2-nitroxyethyl)-5,6,7,8-tetrahydronaphth-1-yl}prop-2-enoate The expected product is obtained according to the process described in Example 1, stage C, starting with the compound described in the preceding stage.

EXAMPLE 13

3-{6-[(4-Chlorophenylsulfonyl)amino]-2-(2-nitroxyethyl)-5,6,7,8-tetrahydronaphth-1-yl}prop-2-enoic acid The expected product is obtained according to the process described in Example 2, stage B, starting with the compound described in Example 12.

EXAMPLE 14

Methyl 3-{6-[(4-chlorophenylsulfonyl)amino]-2-(2-nitrosooxyethyl)-5,6,7,8-tetrahydronaphth-1-yl}propanoate The expected product is obtained according to the process described in Example 1, stage C, using the compound described in Example 1, stage A, as starting material and replacing the tetrabutylammonium nitrate by tert-butyl nitrite.

EXAMPLE 15

3-{6-[(4-Chlorophenylsulfonyl)amino]-2-(2-nitrosoxyethyl)-5,6,7,8-tetrahydronaphth-1-yl}propionic acid The expected product is obtained according to the process described in Example 2, starting with the compound described in Example 14.

EXAMPLE 16

Methyl 3-{6-[(4-chlorophenylsulfonyl)amino]-3-(2-nitroxyethyl)-5,6,7,8-tetrahydronaphth-1-yl}prop-2-enoate The expected product is obtained according to the process described in Example 12, starting with the compound described in preparation E.

EXAMPLE 17

3-{6-[(4-Chlorophenylsulfonyl)amino]-3-(2-nitrosoxyethyl)-5,6,7,8-tetrahydronaphth-1-yl}prop-2-enoic acid The expected product is obtained according to the process described in Example 2, starting with the compound described in Example 16.

EXAMPLE 18

Methyl 3-{6-[(4-chlorophenylsulfonyl)amino]-3-(3-nitroxypropyl)-5,6,7,8-tetrahydronaphth-1-yl}propanoate The expected product is obtained according to the process described in Example 5, starting with the compound described in preparation F.

EXAMPLE 19

3-{6-[(4-Chlorophenylsulfonyl)amino]-3-(3-nitroxypropyl)-5,6,7,8-tetrahydronaphth-1-yl}propionic acid The expected product is obtained according to the process described in Example 2, starting with the compound described in Example 18.

EXAMPLE 20

Ethyl 3-{6-[(4-chlorophenylsulfonyl)amino]-3-(2-nitroxyethyl)-5,6,7,8-tetrahydronaphth-1-yl}carboxylate The expected product is obtained according to the process described in Example 1, starting with the compound described in preparation G.

EXAMPLE 21

3-{6-[(4-Chlorophenylsulfonyl)amino]-3-(2-nitroxyethyl)-5,6,7,8-tetrahydronaphth-1-yl}carboxylic acid The expected product is obtained according to the process described in Example 2, starting with the compound described in Example 20.

EXAMPLE 22

Methyl 3-{6-[(4-chlorophenylsulfonyl)amino]-2-(2-nitroxyethoxy)-5,6,7,8-tetrahydronaphth-1-yl}propanoate The expected product is obtained according to the process described in Example 1, starting with the compound described in preparation H.

EXAMPLE 23

3-{6-[(4-Chlorophenylsulfonyl)amino]-2-(2-nitroxyethoxy)-5,6,7,8-tetrahydronaphth-1-yl}propionic acid The expected product is obtained according to the process described in Example 2, starting with the compound described in Example 22.

EXAMPLE 24

Methyl 3-{6-[(4-chlorophenylsulfonyl)amino]-2,3-bis(2-nitroxyethyl)-5,6,7,8-tetrahydronaphth-1-yl}propanoate The expected product is obtained according to the process described in Example 1, starting with the compound described in preparation I, taking care to follow the stoichiometry.

EXAMPLE 25

3-{6-[(4-Chlorophenylsulfonyl)amino]-2,3-bis(2-nitroxyethyl)-5,6,7,8-tetrahydronaphth-1-yl}propionic acid The expected product is obtained according to the process described in Example 2, starting with the compound described in Example 24.

EXAMPLE 26

2-Nitroxyethyl 3-{6-[(4-chlorophenylsulfonyl)amino]-2-(2-nitroxyethyl)-5,6,7,8-tetrahydronaphth-1-yl}propanoate The expected product is obtained according to the process described in Example 1, starting with the compound described in preparation J, taking care to follow the stoichiometry.

EXAMPLE 27

Methyl 3-{6-[(4-chlorophenylsulfonyl)amino]-2-(2-nitroxyethyl)-5,6,7,8-tetrahydronaphth-1-yl}propanoate The expected product is obtained according to the process described in Example 1, starting with the compound described in preparation K.

EXAMPLE 28

3-{6-[(4-Chlorophenylsulfonyl)amino]-2-(2-nitroxyethyl)-5,6,7,8-tetrahydronaphth-1-yl}propionic acid The expected product is obtained according to the process described in Example 2, starting with the compound described in Example 27.

EXAMPLE 29

Methyl 3-{6-[(4-fluorophenylsulfonyl)amino]-2-(2-nitroxyethyl)-5,6,7,8-tetrahydronaphth-1-yl}propanoate The expected product is obtained according to the process described in Example 1, starting with the compound described in preparation L.

EXAMPLE 30

3-{6-[(4-fluorophenylsulfonyl)amino]-2-(2-nitroxyethyl)-5,6,7,8-tetrahydronaphth-1-yl}propionic acid The expected product is obtained according to the process described in Example 2, starting with the compound described in Example 29.

EXAMPLE 31

Methyl 3-[6-toluylsulfonylamino-2-(2-nitroxyethyl)-5,6,7,8-tetrahydronaphth-1-yl]propanoate The expected product is obtained according to the process described in Example 1, starting with the compound described in preparation M.

EXAMPLE 32

3-[6-Toluylsulfonylamino-2-(2-nitroxyethyl)-5,6,7,8-tetrahydronaphth-1-yl]propionic acid The expected product is obtained according to the process described in Example 2, starting with the compound described in Example 31.

EXAMPLE 33

Methyl 3-{5-[2-[(4-chlorophenylsulfonyl)amino]ethyl]-2-(2-nitroxyethyl)-5,6,7,8-tetrahydronaphth-1-yl}propanoate The expected product is obtained according to the process described in Example 1, starting with the compound described in preparation N.

EXAMPLE 34

3-{5-[2-[(4-Chlorophenylsulfonyl)amino]-ethyl]-2-(2-nitroxyethyl)phenyl}propionic acid The expected product is obtained according to the process described in Example 2, starting with the compound described in Example 33.

EXAMPLE 35

Methyl 3-{5-[2-[(4-chlorophenyl-sulfonyl)amino]ethyl]-3-(2-nitroxyethyl)-phenyl}propanoate The expected product is obtained according to the process described in Example 3, starting with the compound described in preparation O.

EXAMPLE 36

3-{5-[2-[(4-Chlorophenylsulfonyl)amino]-ethyl]-3-(2-nitroxyethyl)phenyl}propionic acid The expected product is obtained according to the process described in Example 2, starting with the compound described in Example 35.

Pharmacological Study of the Derivatives of the Invention

EXAMPLE 37

Platelet aggregation in man

Venous blood is obtained from human volunteers who have not taken any aspirin for at least 14 days prior to the experiment. The blood is taken onto sodium citrate (0.109 M) (1 vol. of citrate by 9 vol. of blood). The platelet-rich plasma (PRP) is obtained after centrifugation (20° C.) at 200×g for 10 minutes. The number of platelets is, on average, 250,000 PL/mm$^3$. The PRP is stored at room temperature until the time of the test and is used within 2 hours of the blood being taken. The antagonists are tested according to the procedure described in Example 19, using U 46619 at a concentration of 0.3 $\mu$M. The compounds of the invention inhibit platelet aggregation induced by the TXA$_2$ agonist, U 46619. The IC$_{50}$ of the compounds of Examples 2 and 4 are equal to 140 nM. This value indicates that the compounds of the invention are powerful anti-platelet-aggregating agents acting on the TXA$_2$ route.

EXAMPLE 38

Determination of the pA$_2$ Values of the Antagonists Towards TXA$_2$ on Rabbit Saphene Vein New Zealand rabbits (2.5 kg) are exsanguinated under anesthesia (pentobarbital, 30 mg/kg) and the saphene veins are rapidly removed and cut into 3-mm rings. These rings are mounted between two hooks in tanks thermostatically adjusted to 37° C., containing physiological saline (composition in mM: 118 NaCl; 25 NaHCO$_3$; 10 glucose; 4.7 KCl; 1.25 CaCl$_2$; 1.19 MgSO$_4$; 1.14 KHPO$_4$).

The physiological saline is bubbled with a mixture of 95% O$_2$/5% CO$_2$. The lower hook constitutes the fixed point whereas the upper hook is connected to an isometric force sensor. The tissues are placed under a base tension of 1 gram. The pharmacological substances studied are prepared immediately before use. The drugs are dissolved in water or in dimethyl sulfoxide.

After mounting, the preparations are left to stand for 90 minutes, with rinsing carried out every 30 minutes. After readjustment of the base tension, a contraction by a single dose of the $TXA_2$ agonist, U 46619 at $10^{-5}$ M, is induced in order to regularize the following contractions. After washing and returning to the base line, a first effect/concentration curve is produced by addition of cumulative doses of U 46619 ($10^{-9}$ M to $10^{-5}$ M; the spacing between the doses is a half-log). This first experiment allows the "control" 50% effective concentration ($EC_{50}$) to be calculated.

This $EC_{50}$ is calculated routinely in the following way: the tension values are first converted into percentages relative to the maximum effect and these percentages are then plotted on a graph with the percentages on the Y-axis and the log (concentration) values on the X-axis. A linear regression is then carried out on the points between 10% and 90% (which corresponds to the linear part of the sigmoidal curve). The concentration corresponding to the half-maximal effect (50%) can readily be calculated using the parameters of the straight line. After washing and returning to the base line, the organ is placed in contact with the antagonist (8 different concentrations for each organ) for 20 minutes. A second effect/concentration curve is thus produced in the presence of the antagonist and the "treated" $EC_{50}$ can then be calculated. This thus provides all the elements which allow the $pA_2$ (competitive antagonism) or $pD_2$ (non-competitive angatonism) to be calculated.

The $pA_2$ (which represents the negative logarithm of the antagonist concentration in the presence of which twice as much antagonist is needed in order to obtain the same effect) is determined by plotting on a graph the values of log (L/1-1) against log (antagonist concentration) with L=effect in the presence of antagonist and I=control effect.

During this test, the $pA_2$ values of the compounds of the invention are as follows:

Example 2: 9.5
Example 6: 9.8

These values indicate that the compounds of the invention are powerful vascular TP-receptor antagonists.

EXAMPLE 39

Determination of the Non-Endothelium-Dependent Relaxations in Rabbit Saphene Vein Rabbit saphene veins are prepared and mounted as described in the above example. After stabilization, a contraction with KCl (60 mM) is induced. During this contraction, increasing concentrations of the substances of the invention are administered and the relaxations resulting therefrom are noted, which allows a 50% effective relaxant concentration ($IC_{50}$) to be calculated. It is calculated as described in the above example.

For the substances of the invention, $IC_{50}$ values below were obtained:

Example 2: 10 μM
Example 6: 7.7 μM

These values indicate that the NO released by our substances induces relaxation of the veins. This was confirmed using a selective inhibitor of guanylate cyclase, ODQ, which is capable of inhibiting relaxations, showing that they are due to the production of cyclic GMP, the mediator of the relaxations induced by NO.

EXAMPLE 40

Pharmaceutical Composition

Preparation formula for 1000 tablets containing a 100 mg dose:

Compound of example 2 . . . 10 g
hydroxypropylcellulose . . . 2 g
wheat starch . . . 10 g
lactose . . . 100 g
magnesium stearate . . . 3 g
talc . . . 3 g

We claim:

1. A compound selected from those of formula (I)

(I)

$$R_1-\underset{\underset{R_3}{|}}{\overset{\overset{R_2}{|}}{C}}-(CH_2)_n-(X)_p-\underset{\text{(ring)}}{\text{}}-(CH_2)_q-(CH)-R_6$$

$$(CH-CH)_m-CO-R_c$$
$$\underset{R_a}{|}\ \underset{R_b}{|}$$

$$-(CH_2)_r-NH-SO_2-\underset{\text{(ring)}}{\text{}}\overset{R_d}{\underset{R_e}{}}$$

in which:

$R_a$ and $R_b$, which may be identical or different, represent a hydrogen atom or a linear or branched ($C_1$–$C_6$) alkyl group, or alternatively $R_a$ and $R_b$ together form a bond, $R_c$, represents a hydroxyl group, a linear or branched ($C_1$–$C_6$) alkoxy group (optionally substituted with an —O—$NO_2$, —O—NO, or —S—NO group), or an amino group (optionally substituted with one or two identical or different, linear or branched ($C_1$–$C_6$) alkyl groups, or with an optionally substituted phenyl group), $R_1$ represents a hydrogen atom or an —O—$NO_2$, —O—NO, or —S—NO group, $R_2$ and $R_3$, which may be identical or different, represent a hydrogen atom or a linear or branched ($C_1$–$C_6$) alkyl group or an optionally substituted phenyl group, X represents an oxygen atom or an —NH—CO— group, m represents 0 or 1, n represents an integer such that $0 \leq n \leq 6$, p represents 0 or 1, $R_4$ represents a hydrogen atom, a linear or branched ($C_1$–$C_6$) alkyl group (optionally substituted with a hydroxyl group), an optionally substituted phenyl group, or a group:

$$R'_1-\underset{\underset{R'_3}{|}}{\overset{\overset{R'_2}{|}}{C}}-(CH_2)_{n'}-(X')_{p'}-$$

in which:

$R'_1$, represents a hydrogen atom or a group: —O—$NO_2$—, —O—NO, or —S—NO, $R'_2$ and $R'_3$, which may be identical or different, represent a hydrogen atom or a linear or branched ($C_1$–$C_6$) alkyl group or an optionally substituted phenyl group, X' represents an oxygen atom or an —NH—CO— group, n' represents an integer such that $0 \leq n' \leq 6$, p' represents 0 or 1, $R_5$ represents a hydrogen atom or a linear or branched ($C_1$–$C_6$) alkyl group, $R_6$ represents a hydrogen atom or a linear or branched ($C_1$–$C_6$) alkyl group, or alternatively $R_5$ and $R_6$ together form a chain —$(CH_2)_t$— in which t represents 1 or 2, q represents 0, 1, or 2, r represents an integer such that $0 \leq r \leq 6$, $R_d$ and $R_e$, which may be identical or different, represent a hydrogen atom, a halogen atom, a linear or branched ($C_1$–$C_6$) alkyl group, a linear or branched ($C_1$–$C_6$) alkoxy group, a hydroxyl group, or a linear or branched ($C_1$–$C_6$) trihaloalkyl group, it being understood that at least one —O—$NO_2$, —O—NO, or —S—NO group is present in $R_1$, $R_4$ or $R_c$, and the geometrical and optical isomers thereof and the addition salts thereof with a pharmaceutically acceptable acid or base.

2. A compound of claim 1, wherein $R_1$ represents —O—$NO_2$, —O—NO, or —S—NO.

3. A compound of claim 1, wherein $R_a$ and $R_b$ simultaneously represent a hydrogen atom and m is equal to 1.

4. A compound of claim 1, wherein $R_5$ and $R_6$ together form a chain —$(CH_2)_t$—.

5. A compound of claim 1, wherein $R_4$ represents a hydrogen atom.

6. A compound of claim 1, wherein p is equal to 0.

7. A compound of claim 1, wherein $R_c$ represents a hydroxyl group or a linear or branched ($C_1$–$C_6$) alkoxy group.

8. A compound of claim 1, wherein $R_d$ represents a halogen atom when $R_e$ represents a hydrogen atom.

9. A compound of claim 1, wherein $R_1$ represents an —O—$NO_2$ group when p is equal to 0, $R_a$ and $R_b$ each represent a hydrogen atom when m is equal to 1, $R_4$ represents a hydrogen atom, $R_5$ and $R_6$ together form a chain —$(CH_2)_t$ with t equal to 2 when q is equal to 1, and r is equal to 0, $R_d$ represents a halogen atom when $R_e$ represents a hydrogen atom and $R_c$ represents a hydroxyl group or a linear or branched ($C_1$–$C_6$) alkoxy group.

10. A compound of claim 1, which is selected from 3-{6-[(4-chlorophenylsulfonyl)amino]-2-(2-nitroxyethyl)-5, 6,7,8-tetrahydronaphth-1-yl}propionic acid, and addition salts thereof with a pharmaceutically-acceptable base.

11. A compound of claim 1, which is selected from 3-{6-[(4-chlorophenylsulfonyl)amino]-3-(2-nitroxyethyl)-5, 6,7, 8-tetrahydronaphth-1-yl}propionic acid, and addition salts thereof with a pharmaceutically-acceptable base.

12. A compound of claim 1, which is selected from 3-{6-[(4-chlorophenylsulfonyl)amino]-3-nitroxymethyl-5, 6,7,8-tetrahydronaphth-1-yl}propionic acid, and addition salts thereof with a pharmaceutically-acceptable base.

13. A process for the preparation of a compound of claim 1, wherein p=p'=0 which uses a s starting material a compound of formula (II):

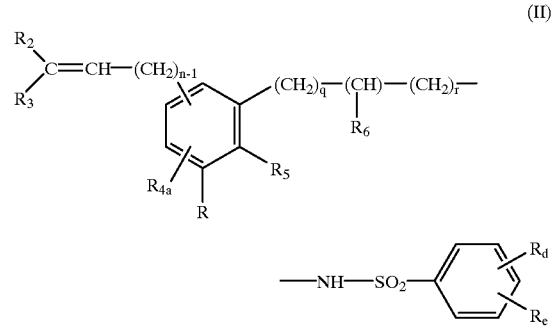

in which:

$R_d$, $R_e$, $R_2$, $R_3$, $R_5$, $R_6$, n, q and r have the same meanings as in claim 1, $R_{4a}$ represents a hydrogen atom, a linear or branched ($C_1$–$C_6$) alkyl group (optionally substituted with a hydroxyl group), an optionally substituted phenyl group, or a group

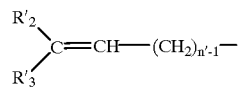

in which $R'_2$, $R'_3$ and n' have the same meanings as in claim 1, and R represents —$CH_2$—$CH_2$—$CO_2R'$, or —$CO_2R'_c$ (in which $R'_c$ represents a linear or branched ($C_1$–$C_6$) alkyl group optionally substituted with a hydroxyl group), which compound is subjected to an oxidizing treatment, to give a compound of formula (III):

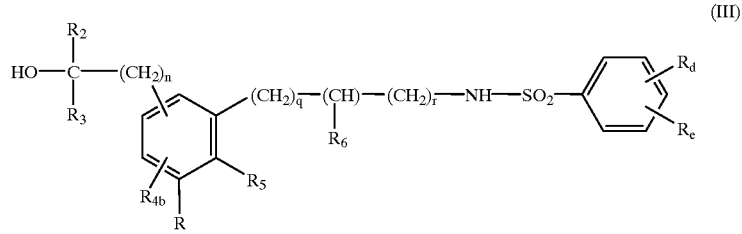

in which:

R, $R_d$, $R_e$, $R_2$, $R_3$, $R_5$, $R_6$, n, q and r have the same meanings as above, $R_{4b}$ represents a hydrogen atom, a linear or branched ($C_1$–$C_6$) alkyl group (optionally substituted with a hydroxyl group), an optionally substituted phenyl group, or a group

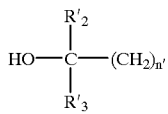

in which R'$_2$, R'$_3$ and n' have the same meanings as above, which compound of formula (III) is optionally converted, when R represents a group —CO$_2$Alk, into the corresponding aldehyde and then subjected to a Wittig reaction to give a compound of formula (III) in which the group R is replaced by the group —CH=CH—CO$_2$R'$_c$, which compound of formula (III):

either has its hydroxyl group(s) converted into an OTs group (in which Ts represents the tosyl group) or into a bromine atom, and is subjected to the action of tetrabutylammonium nitrate or silver nitrate, to give a compound of formula (I/a), which is a specific case of the compounds of formula (I):

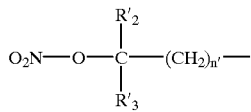

in which R'$_2$, R'$_3$ and n' have the same meanings as above, and

R'$_{c1}$ represents an alkyl group optionally substituted with an —O—NO$_2$ group, or is reacted with tert-butyl nitrite to give a compound of formula (I/b), which is a specific case of the compounds of formula (I):

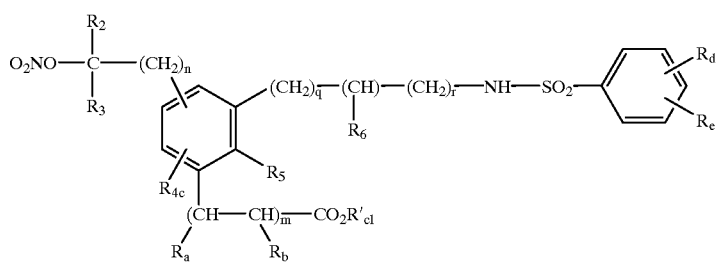

(I/a)

in which:

R$_2$, R$_3$, R$_5$, R$_6$, R$_a$, R$_b$, R$_d$, R$_e$, m, n, q and r have the same meanings as in claim 1, and R$_{4c}$ represents a hydrogen atom, a linear or branched (C$_1$–C$_6$) alkyl group, an optionally substituted phenyl group or a group,

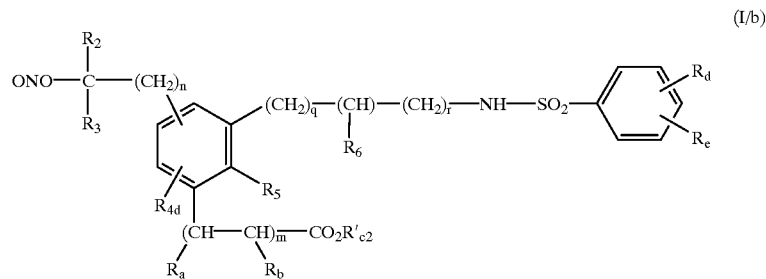

(I/b)

in which

R$_2$, R$_3$, R$_5$, R$_6$, R$_a$, R$_b$, R$_d$, m, n, q and r have the same meanings as above, and R$_{4d}$ represents a hydrogen atom, a linear or branched (C$_1$–C$_6$) alkyl group, an optionally substituted phenyl group or a group,

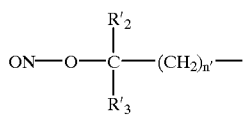

in which R'$_2$, R'$_3$ and n' have the same meanings as above, and $R'_{c2}$ represents an alkyl group optionally substituted with an —O—NO group, which compounds of formula (I/a) or (I/b) have the ester function converted, if so desired, into the corresponding acid or amide function, which compounds can, where appropriate, be purified according to a standard purification technique, have their isomers separated, where appropriate, according to a standard separation technique, are converted, if so desired, into addition salts thereof with a pharmaceutically-acceptable acid or base.

14. A process for the preparation of a compound as claimed in claim 1, wherein p or p' is equal to 1 and X and X' represent —NH—CO—, in which the starting material used is a compound of formula (IV):

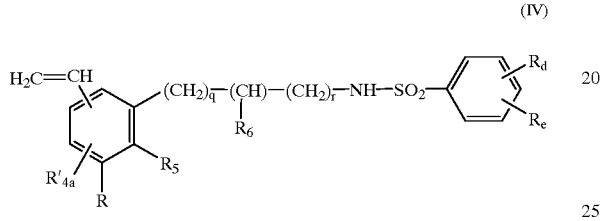

(IV)

in which:

$R_d$, $R_e$, $R_5$, $R_6$, q and r have the same meanings as in formula (I),

R represents —$CH_2$—$CH_2$—$CO_2R'_c$, or —$CO_2R'_c$ (in which R'c represents a linear or branched ($C_1$–$C_6$) alkyl group optionally substituted with a hydroxyl group), $R'_{4a}$ represents a hydrogen atom, a linear or branched ($C_1$–$C_6$) alkyl group (optionally substituted with a hydroxyl group), an optionally substituted phenyl group, or a vinyl group, the vinyl group(s) of which is (are) converted into formyl group(s) and then into corresponding carboxyl group(s), which compound is reacted with an amine of formula (V):

(V)

in which:

$R_2$, $R_3$ and n have the same meanings as in formula (I) and Y represents a sulfur or oxygen atom, to give a compound of formula (VI):

in which:

R, $R_d$, $R_e$, $R_5$, $R_2$, $R_3$, $R_6$, Y, n, q and r have the same meanings as above, $R'_{4b}$ represents a hydrogen atom, a linear or branched ($C_1$–$C_6$) alkyl group, (optionally substituted with a hydroxyl group), an optionally substituted phenyl group or a group

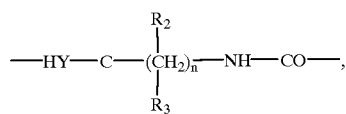

which compound of formula (VI) is optionally converted, when R represents a group —$CO_2$Alk, into the corresponding aldehyde and then undergoes a Wittig reaction to give a compound of formula (VI) in which the group R is replaced by the group —CH=CH—$CO_2R'_c$, which compound of formula (VI):

either has its hydroxyl group(s) converted into an OTs group (in which Ts represents the tosyl group) or into a bromine atom, and is subjected to the action of tetrabutylammonium nitrate or silver nitrate, to give a compound of formula (I/c), which is a specific case of the compounds of formula (I):

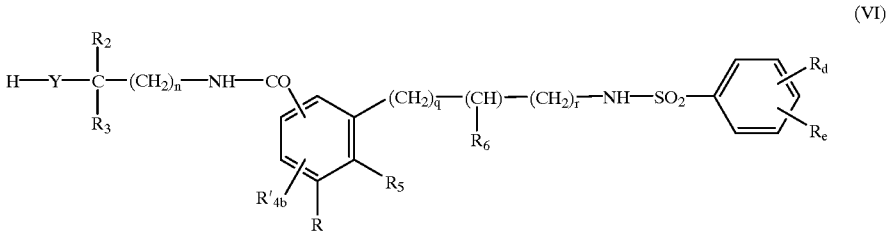

(VI)

(I/c)

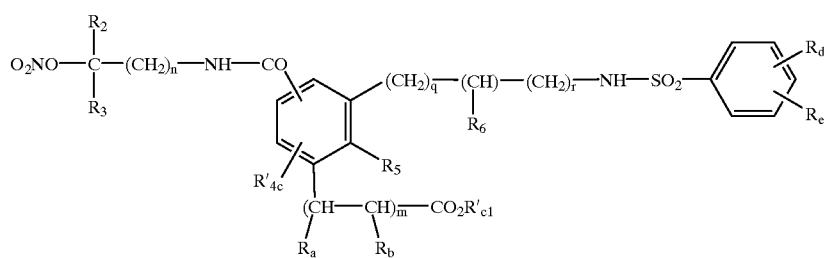

in which:

R$_2$, R$_3$, R$_5$, R$_6$, R$_a$, R$_b$, R$_d$, R$_e$, m, n, q and r have the same meanings as in formula (I), and R'$_{4c}$ represents a hydrogen atom, a linear or branched (C$_1$-C$_6$) alkyl group (optionally substituted with an —O—NO$_2$ group), an optionally substituted phenyl group or a group,

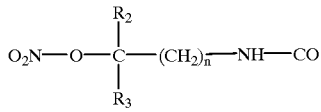

in which R$_2$, R$_3$ and n have the same meanings as above, and

R'$_{c1}$ represents an alkyl group optionally substituted with an —O—NO$_2$ group, or is reacted with tert-butyl nitrite to give a compound of formula (I/d), which is a specific case of the compounds of formula (I):

O—NO group), an optionally substituted phenyl group or a group,

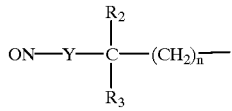

in which Y, R$_2$, R$_3$ and n have the same meanings as above and R'$_{c2}$ represents an alkyl group optionally substituted with an —O—NO group, which compounds of formula (I/c) or (I/d) have their ester function converted, if so desired, into the corresponding acid or amide function, which can, where appropriate, be purified according to a standard purification technique, have their isomers separated, where appropriate, according to a standard separation technique, are converted, if so desired, into addition salts thereof with a pharmaceutically-acceptable acid or base.

(I/d)

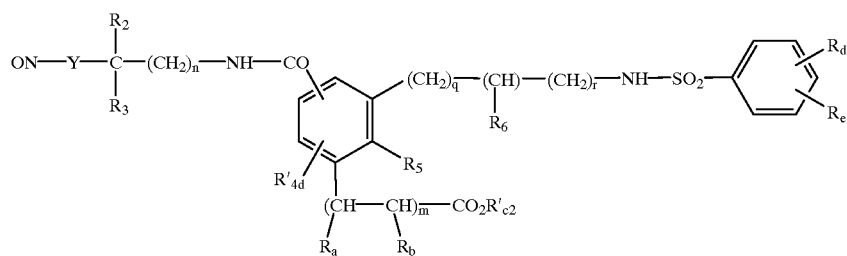

in which:

Y, R$_2$, R$_3$, R$_5$, R$_6$, R$_a$, R$_b$, R$_d$, m, n, q and r have the same meanings as above, and R'$_{4d}$ represents a hydrogen atom, a linear or branched (C$_1$-C$_6$) alkyl group (optionally substituted with an 15. A process for the preparation of a compound as claimed in claim 1 wherein X represents an oxygen atom, in which the starting material used is a compound of formula (VII):

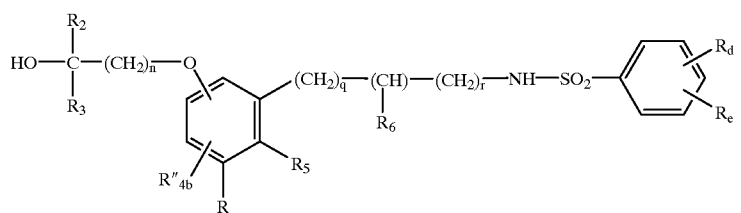
(VII)

in which:

$R_2$, $R_3$, $R_5$, $R_d$, $R_e$, r, q and n are as defined in formula (I), R represents a group

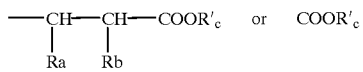

in which $R'_c$ represents a linear or branched ($C_1$–$C_6$) alkyl group optionally substituted with a hydroxyl group and $R_a$ and $R_b$ are as defined in formula (I), and $R'_{4b}$ represents a hydrogen atom, a linear or branched ($C_1$–$C_6$) alkyl group, an optionally substituted phenyl group, or a group

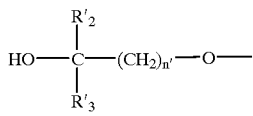

in which n', $R'_2$ and $R'_3$ are as defined in formula (I)), which compound of formula (VII):

either has its hydroxyl group(s) converted into an OTs group (in which Ts represents a tosyl group) or into a bromine atom, and is subjected to the action of tetrabutylammonium nitrate or silver nitrate, to give a compound of formula (I/e), which is a specific case of the compounds of formula (I)

in which:

$R_2$, $R_3$, $R_5$, $R_6$, $R_a$, $R_b$, $R_d$, $R_e$, m, n, q and r have the same meanings as in formula (I), and $R''_{4c}$ represents a hydrogen atom, an alkyl group, an optionally substituted phenyl group, or a group in which

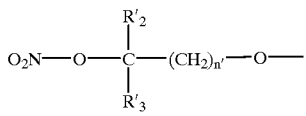

$R'_2$, $R'_3$ and n' have the same meanings as above and $R'_{c1}$ represents an alkyl group optionally substituted with an —$ONO_2$ group, or is reacted with tert-butyl nitrite to give a compound of formula (I/f), which is a specific case of the compounds of formula (I):

(I/e)

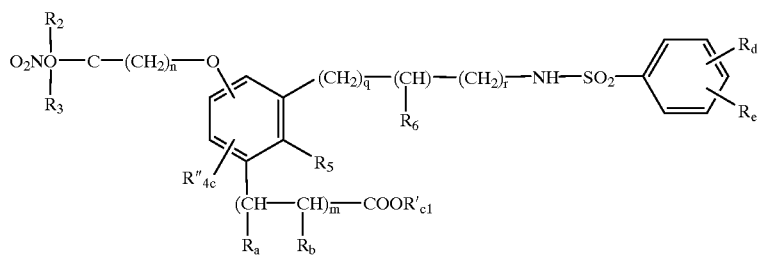

(I/f)

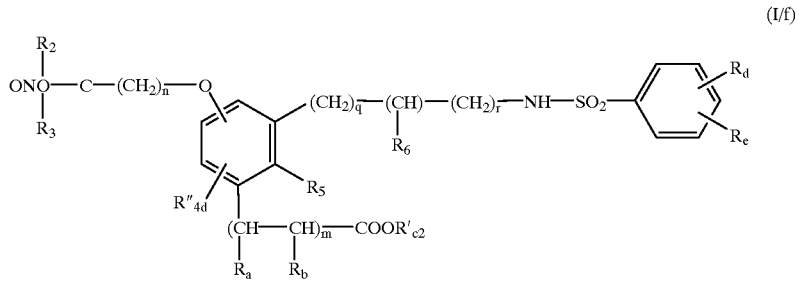

in which:

$R_2$, $R_3$, $R_5$, $R_6$, $R_a$, $R_b$, $R_d$, $R_e$, n, m, q and r have the same meanings as in formula (I), $R''_{4d}$ represents a hydrogen atom, an alkyl group, an optionally substituted phenyl group, or a group in which

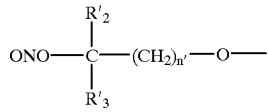

$R'_2$, $R'_3$ and n' have the same meanings as above and $R'_{c2}$ represents an alkyl group optionally substituted with an —O—NO group, which compound of formula (I/e) or (I/f) has its ester function converted, if so desired, into the corresponding acid or amide function, which compound can, where appropriate, be purified according to a standard purification technique, has its isomers separated, where appropriate, according to a standard separation technique, is converted, if so desired, into addition salts thereof with a pharmaceutically-acceptable acid or base.

16. A pharmaceutical composition containing, as active principle, at least one compound as claimed in claim 1 in combination with one or more pharmaceutically-acceptable excipients or vehicles.

17. A pharmaceutical composition as claimed in claim 16, wherein the compound is useful as a $TXA_2$-receptor antagonist and as an NO donor.

18. Method for the treatment of a living animal body afflicted with a condition, which is improved by administration of a $TXA_2$-receptor antagonist and/or NO donor, comprising the step of administering to the living animal body an effective amount of a compound of claim 1.

19. Method for the treatment of a living animal body afflicted with a condition, which is improved by administration of a $TXA_2$-receptor antagonist and/or NO donor, comprising the step of administering to the living animal body an effective amount of a compound of claim 10.

20. Method for the treatment of a living animal body afflicted with a condition, which is improved by administration of a $TXA_2$-receptor antagonist and/or NO donor, comprising the step of administering to the living animal body an effective amount of a compound of claim 11.

21. Method for the treatment of a living animal body afflicted with a condition, which is improved by administration of a $TXA_2$-receptor antagonist and/or NO donor, comprising the step of administering to the living animal body an effective amount of a compound of claim 12.

* * * * *

UNITED STATES PATENT AND TRADEMARK OFFICE
CERTIFICATE OF CORRECTION

PATENT NO. : 6,013,667
DATED : Jan. 11, 2000
INVENTOR(S) : G. Lavielle, B. Cimetiere, T. Verbeuren, S. Simonet, J.J. Descombes It is certified that error appears in the above-indentified patent and that said Letters Patent is hereby corrected as shown below:

Column 1, line 37: After the word "properties", insert the following: -- (Moncada and Higgs, N. Engl.J. Med., 329,2002-2012, 1993). --.

Column 1, line 37: "Nitro derivatives, ...... should begin a new paragraph.

Column 4, line 53: Formula (III) should read as follows:

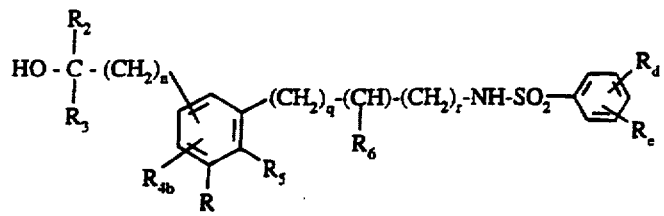

Column 22, line 39: Delete the number "8" before "C4-"

Column 29, line 17: Insert a -- hyphen (-) -- between the words "pharmaceutically" and "accept-".

Column 29, line 66: "a s" should read -- as --.

UNITED STATES PATENT AND TRADEMARK OFFICE
CERTIFICATE OF CORRECTION

PATENT NO.  : 6,013,667
DATED       : Jan. 11, 2000
INVENTOR(S) : G. Lavielle, B. Cimetiere, T. Verbeuren, S. Simonet, J.J. Descombes It is certified that error appears in the above-indentified patent and that said Letters Patent is hereby corrected as shown below:

Column 30, line 21:    "$R_4a$" should read:  -- $R_{4a}$ --.

Column 30, line 34:    "$-CO_2R'$," should read: -- $-CO_2R'_c$ --.

Column 31, line 67:    Insert a -- comma (,) -- after the word "group" first instance.

Column 34, line 14:    Insert a -- comma (,) -- after the word "group" first instance.

Column 36, line 15:    At the end of the line, insert a -- comma (,) -- after the word "group".

Signed and Sealed this

Twenty-fourth Day of October, 2000

Q. TODD DICKINSON

*Attest:*

*Attesting Officer*               *Director of Patents and Trademarks*